United States Patent [19]

Berg

[11] Patent Number: 5,094,725
[45] Date of Patent: * Mar. 10, 1992

[54] SEPARATION OF M-XYLENE FROM O-XYLENE BY EXTRACTIVE DISTILLATION WITH ESTERS

[75] Inventor: Lloyd Berg, 1314 S. Third Ave., Bozeman, Mont. 59715

[73] Assignee: Lloyd Berg, Bozeman, Mont.

[*] Notice: The portion of the term of this patent subsequent to Jun. 30, 2004 has been disclaimed.

[21] Appl. No.: 680,351

[22] Filed: Apr. 4, 1991

[51] Int. Cl.$^5$ .................. B01D 3/40; C07C 7/08
[52] U.S. Cl. .................. 203/60; 585/866
[58] Field of Search .......... 203/60, 51; 585/805, 585/866

[56] References Cited

U.S. PATENT DOCUMENTS

| | | | |
|---|---|---|---|
| 2,456,566 | 12/1948 | Lake et al. | 203/60 |
| 2,763,604 | 9/1956 | Dorsey et al. | 203/60 |
| 2,957,811 | 10/1960 | Geiser | 203/60 |
| 3,227,632 | 1/1966 | Schmalenbach et al. | 203/58 |
| 3,684,665 | 8/1972 | Abe et al. | 203/60 |
| 4,488,937 | 12/1984 | Berg et al. | 203/60 |
| 4,676,872 | 6/1987 | Berg et al. | 203/56 |
| 4,676,875 | 6/1987 | Berg et al. | 585/808 |
| 4,738,755 | 4/1988 | Berg et al. | 203/60 |
| 4,822,947 | 4/1989 | Berg et al. | 203/58 |
| 5,019,217 | 5/1991 | Berg et al. | 203/51 |

Primary Examiner—Wilbur Bascomb, Jr.

[57] ABSTRACT m-Xylene is difficult to separate from o-xylene by conventional distillation or rectification because of the close proximity of their boiling points. m-Xylene can be readily separated from o-xylene by using extractive distillation in which the agent is an aliphatic ester. Typical examples of effective agents are diethyl maleate, diethyl malonate or 2-ethyl hexyl acetate.

1 Claim, No Drawings

SEPARATION OF M-XYLENE FROM O-XYLENE BY EXTRACTIVE DISTILLATION WITH ESTERS

FIELD OF THE INVENTION

This invention relates to a method for separating m-xylene from o-xylene using certain aliphatic esters as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

m-Xylene, B.P.=139.1° C. and o-xylene, B.P.=144.4° C. have a relative volatility of 1.12 and are difficult to separate by rectification. Extractive distillation would be an attractive method of effecting the separation of xylenes if agents can be found that (1) will enhance the relative volatility between the xylenes and (2) are easy to recover from the xylenes, that is, form no azeotrope with xylene and boil sufficiently above xylene to make the separation by rectification possible with only a few theoretical plates.

The advantage of using extractive distillation in this separation can be seen from the data shown in Table 1 below.

TABLE 1

Theoretical and Actual Plates Required vs. Relative Volatility for Xylene Separation

| Relative Volatility | Theoretical Plates Required At Total Reflux, 95% Purity | Actual Plates Required, 75% Eff. |
|---|---|---|
| 1.12 | 52 | 70 |
| 1.20 | 33 | 44 |
| 1.25 | 27 | 36 |
| 1.30 | 23 | 31 |
| 1.35 | 20 | 27 |
| 1.40 | 18 | 24 |

The relative volatility of m-xylene to o-xylene is 1.12 and thus require 52 theoretical plates for separation by conventional rectification at total reflux. Plates possessing an efficiency of 75% are commonly employed and thus about 70 actual plates are required, clearly a difficult separation. Several of the agents that I have discovered yield a relative volatility of 1.25 which would reduce the plate requirement to only 36.

Extractive distillation typically requires the addition of an equal amount to twice as much extractive agent as the m-xylene and o-xylene on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with the xylenes otherwise it will form a two-phase azeotrope with the formic acid in the recovery column and some other method of separation will have to be employed.

Previous work on the separation of xylenes has been reported. Dorsey, U.S. Pat. No. 2,763,604 used aromatic nitriles to separate xylenes from other aromatic hydrocarbons. He got very little separation of m-xylene from o-xylene. Schmalenbach, U.S. Pat. No. 3,227,632 used anhydrous propylene carbonate to separate xylenes from other aromatic hydrocarbons but there was not much separation of one xylene from another xylene. Geiser, U.S. Pat. No. 2,957,811 used carboxyamides such as dimethylformamide to separate mixtures comprising toluene, ethylbenzene and the xylenes. There was not much change in the ratio of m-xylene to o-xylene with this agent.

Previous work on the separation of m-xylene from o-xylene by extractive distillation has been reported by Berg et al. U.S. Pat. No. 4,488,937 described the use of sulfolane; U.S. Pat. No. 4,585,526 used ether-alcohols; U.S. Pat. No. 4,673,465 employed polychloro compounds; U.S. Pat. No. 4,676,872 described adiponitrile; U.S. Pat. No. 4,676,875 reported dimethylformamide and U.S. Pat. No. 4,738,755 used benzoates.

OBJECTIVE OF THE INVENTION

The objects of this invention are to provide a process or method of extractive distillation that will enhance the relative volatility of m-xylene to o-xylene in their separation in a rectification column. It is a further object of this invention to identify esters that are stable, can be separated from the xylenes by rectification with relatively few plates and can be recycled to the extractive distillation column with little decomposition.

SUMMARY OF THE INVENTION

The objects of the invention are provided by a process for the separation of m-xylene from o-xylene which entails the use of certain aliphatic esters as the agent in extractive distillation.

DETAILED DESCRIPTION OF THE INVENTION

I have discovered that certain compounds, principally aliphatic esters, either alone or admixed with each other, will effectively increase the relative volatility between m-xylene and o-xylene and permit the separation of m-xylene from o-xylene by rectification when employed as the agent in extractive distillation. Table 2 lists the agents that I have found to be effective. The data in Table 2 was obtained in a vapor-liquid equilibrium still. In every case, the starting material was a mixture of $m$-xylene and $o$-xylene in the ratio of 30%–70%, 50%–50% or 70%–30%. The relative volatilities are listed for each of the agents. The compounds which are effective are hexyl acetate, diethyl maleate, diethyl malonate, 2-ethyl hexyl acetate and ethyl acetoacetate.

Table 3 lists a number of compounds which might have been expected to act favorably in the separation of m-xylene from o-xylene but which failed to yield an effective relative volatility.

Two of the esters whose relative volatilities had been determined in the vapor-liquid equilbrium still were then evaluated in a glass perforated plate rectification column possessing 7.3 theoretical plates and the results listed in Table 4. Diethyl malonate yielded a relative volatility of 1.246 after two hours of operation. 2-Ethyl hexyl acetate yielded a relative volatility of 1.255 after two hours of operation.

TABLE 2

| Effective Agents For Separating m-Xylene From o-Xylene | |
|---|---|
| Compounds | Relative Volatility |
| Hexyl acetate | 1.21 |
| Diethyl maleate | 1.30 |
| Diethyl malonate | 1.24 |
| 2-Ethyl hexyl acetate | 1.26 |
| Ethyl acetoacetate | 1.21 |

TABLE 3

| Ineffective Agents For Separating m-Xylene From o-Xylene | |
|---|---|
| Compounds | Relative Volatility |
| Butyl propionate | 1.18 |
| Butyl butyrate | 1.13 |
| Ethyl caproate | 1.18 |
| Tripropylene glycol | 1.14 |
| Benzyl butyl phthalate | 1.10 |
| 1,5-Pentanediol | 1.17 |
| Tripropylene glycol methyl ether | 1.03 |
| Glcerol triacetate | 1.03 |
| Ethylene glycol diacetate | 1.07 |
| Triethylene glycol diacetate | 1.07 |
| Methyl caproate | 1.19 |
| Isobutyl isobutyrate | 1.10 |
| Ethylene glycol ethyl ether acetate | 1.17 |
| Ethylene glycol butyl ether acetate | 1.11 |
| Methyl amyl acetate | 1.06 |
| Diethylene glycol ethyl ether acetate | 1.13 |
| Phenyl acetate | 1.16 |
| Ethyl phenyl acetate | 1.08 |

TABLE 3-continued

| Ineffective Agents For Separating m-Xylene From o-Xylene | |
|---|---|
| Compounds | Relative Volatility |
| Methyl acetoacetate | 1.17 |
| Isobornyl acetate | 1.11 |
| Ethyl benzoate | 1.04 |
| Methyl heptanoate | 1.17 |
| Ethyl heptanoate | 1.10 |
| Amyl propionate | 1.14 |
| Ethyl valerate | 1.04 |
| Propyl caproate | 1.17 |

TABLE 4

Data From Runs Made In Rectification Column-m-Xylene From o-Xylene

| Agent | Column | Time hrs. | Weight % m-Xylene | Weight % o-Xylene | Relative Volatility |
|---|---|---|---|---|---|
| Diethyl malonate | Overhead | 1 | 65.6 | 34.4 | 1.15 |
| | Bottoms | | 41.2 | 58.8 | |
| Diethyl malonate | Overhead | 1.5 | 70.1 | 29.9 | 1.245 |
| | Bottoms | | 32.6 | 67.4 | |
| Diethyl malonate | Overhead | 2 | 70.6 | 29.6 | 1.246 |
| | Bottoms | | 32.3 | 67.7 | |
| 2-Ethyl hexyl acetate | Overhead | 1 | 68.3 | 31.7 | 1.252 |
| | Bottoms | | 29.4 | 70.6 | |
| 2-Ethyl hexyl acetate | Overhead | 2 | 69.9 | 30.1 | 1.255 |
| | Bottoms | | 30.5 | 69.5 | |
| 2-Ethyl hexyl acetate | Overhead | 3 | 67.8 | 32.2 | 1.240 |
| | Bottoms | | 30.5 | 69.5 | |

THE USEFULNESS OF THE INVENTION

The usefulness or utility of this invention can be demonstrated by referring to the data presented in Tables 2, 3 and 4. All of the successful agents show that m-xylene can be separated from o-xylene by means of extractive distillation in a rectification column and that the ease of separation as measured by relative volatility is considerable.

WORKING EXAMPLES

Example 1

Fifteen grams of m-xylene, 35 grams of o-xylene and forty grams of diethyl malonate were charged to the vapor-liquid equilibrium still and refluxed for thirteen hours. Analysis indicated a vapor composition of 36.8% m-xylene, 63.2% o-xylene; a liquid composition of 32.5% m-xylene, 67.5% o-xylene which is a relative volatility of 1.21.

Example 2

A glass perforated plate rectification column was calibrated with m-xylene and o-xylene which possesses a relative volatility of 1.11 and found to have 7.3 theoretical plates. A solution comprising 150 ml. of m-xylene and 225 ml. of o-xylene was placed in the stillpot and heated. When refluxing began, an extractive agent comprising diethyl malonate was pumped into the column at a rate of 15 ml/min. The temperature of the extractive agent as it entered the column was 95° C. After establishing the feed rate of the extractive agent, the heat input to the m-xylene—o-xylene in the stillpot was adjusted to give a total reflux rate of 40 ml/min. After 1.5 hours of operation, the overhead and bottoms samples of approximately two ml. were collected and analysed by gas chromatography. The overhead analysis was 70.1% m-xylene, 29.9% o-xylene. The bottoms analysis was 32.6% m-xylene, 67.4% o-xylene. Using these compositions in the Fenske equation, with the number of theoretical plates in the column being 7.3, gave an average relative volatility of 1.245 for each theoretical plate. After a total of two hours of continuous operation, samples of overhead and bottoms were again taken and analysed. The overhead analysis was 70.4% m-xylene, 29.6% o-xylene; the bottoms analysis was 32.3% m-xylene, 67.7% o-xylene which is a relative volatility of 1.246.

Example 3

150 ml. of m-xylene and 250 ml. of o-xylene were placed in the stillpot of the 7.3 theoretical plate rectification column and heated. When refluxing began, an extractive agent comprising 2-ethyl hexyl acetate was pumped into the column at a rate of 15 ml/min. The temperature of the extractive agent as it entered the column was 95° C. After establishing the feed rate of the extractive agent, the heat input to the stillpot was adjusted to give a total reflux rate of 40 ml/min. After two hours of operation, overhead and bottoms samples of approximately two ml. were collected and analysed by gas chromatography. The overhead analysis was 69.9% m-xylene, 30.1% o-xylene and the bottoms analysis was 30.5% m-xylene, 69.5% o-xylene. Using these compositions in the Fenske equation, with the number of theoretical plates in the column being 7.3, gave an average relative volatility of 1.255 for each theoretical plate. The data for Examples 2 and 3 is presented in Table 4.

I claim:

1. A method for recovering m-xylene from a mixture of m-xylene and o-xylene which comprises distilling a mixture of m-xylene and o-xylene in the presence of about one part of an extractive agent per part of m-xylene—o-xylene mixture, recovering the m-xylene as overhead product and obtaining the o-xylene and the extractive agent from the stillpot, wherein said extractive agent consists of one material selected from the group consisting of diethyl maleate and diethyl malonate.

* * * * *